(12) United States Patent
McCarter

(10) Patent No.: US 10,639,531 B1
(45) Date of Patent: May 5, 2020

(54) PRACTICE AID DEVICE FOR PERFORMANCE FEEDBACK AND HAND AND FINGER POSITIONING TRAINING DURING SPORTS PLAY

(71) Applicant: Zevon T. McCarter, Temple Terrace, FL (US)

(72) Inventor: Zevon T. McCarter, Temple Terrace, FL (US)

( * ) Notice: Subject to any disclaimer, the term of this patent is extended or adjusted under 35 U.S.C. 154(b) by 0 days.

(21) Appl. No.: 16/460,633

(22) Filed: Jul. 2, 2019

(51) Int. Cl.
*A63B 69/00* (2006.01)
*A63B 23/16* (2006.01)
(Continued)

(52) U.S. Cl.
CPC ........... *A63B 69/00* (2013.01); *A61H 1/0288* (2013.01); *A63B 71/0622* (2013.01); *A61H 2201/149* (2013.01); *A61H 2201/1638* (2013.01); *A61H 2201/1652* (2013.01); *A63B 69/0002* (2013.01); *A63B 69/0071* (2013.01);
(Continued)

(58) Field of Classification Search
CPC . A63B 69/00; A63B 71/0622; A63B 69/0071; A63B 2220/833; A63B 2220/836; A63B 2071/0694; A63B 69/0002; A63B 2220/20; A63B 2220/51; A63B 2102/02; A63B 21/4019; A63B 21/4025; A63B 2209/10; A63B 2071/0633; A63B 21/0004; A63B 21/00189; A63B 21/4021; A63B 23/16; A63B 69/0059; A63B 71/148; A63B 21/00061; A63B 21/00069; A63B 21/055; A63B 21/0552; A63B 21/065; A63B 21/4017; A63B 2220/801;
A61H 1/0288; A61H 2201/149; A61H 2201/1652; A61H 2201/1638; A61H 1/0285; A61H 2201/1215; A61H 2201/165; G06F 3/014; G06F 3/011; G06F 2203/0331; G06F 3/0346; G06F 2203/0335; G06F 3/016; G06F 3/03547; A63F 13/212; A63F 13/285; A61B 5/6825; A61B 5/6826
USPC ................. 473/61, 422, 446, 464, 458, 459; 482/124, 125
See application file for complete search history.

(56) References Cited

U.S. PATENT DOCUMENTS

| | | |
|---|---|---|
| 4,451,044 A | 5/1984 | Elliott, Jr. |
| 4,738,447 A | 4/1988 | Brown |
| (Continued) | | |

OTHER PUBLICATIONS

Raymond Wong, Wilson's Smart Basketball, Tech Mashable, review Mar. 15, 2016, 6 pages, https://mashable.com/2016/03/15/wilson-x-connected-basketball-review/ Mashable, New York, NY, US.
(Continued)

*Primary Examiner* — Nini F Legesse
(74) *Attorney, Agent, or Firm* — Olav M. Underdal; IDP Patent Services

(57) ABSTRACT

A practice aid device includes a control body; a control unit; a plurality of finger control assemblies, each including a rotary assembly with a rotatable spool and a rotary actuator, a control cable, a finger strap, a lateral sensor, a finger cap with a tip tension sensor; front and rear straps for connecting the control body to a forearm of a user; and a touch screen, in order to enable the user to control outward and inward rotation of each rotary actuator and measure control cable extension, finger separation distance, and pulling force.

20 Claims, 7 Drawing Sheets

(51) Int. Cl.
*A63B 71/06* (2006.01)
*A61H 1/02* (2006.01)
*A63B 102/02* (2015.01)

(52) U.S. Cl.
CPC ... *A63B 2071/0694* (2013.01); *A63B 2102/02* (2015.10); *A63B 2220/20* (2013.01); *A63B 2220/51* (2013.01); *A63B 2220/833* (2013.01); *A63B 2220/836* (2013.01)

(56) References Cited

U.S. PATENT DOCUMENTS

| | | | | |
|---|---|---|---|---|
| 4,881,275 | A | * | 11/1989 | Cazares ............... A63B 71/148 2/161.1 |
| 5,149,085 | A | | 9/1992 | Sanchez |
| 5,346,208 | A | | 9/1994 | Wood |
| 5,938,547 | A | | 8/1999 | Gilford |
| 6,141,643 | A | * | 10/2000 | Harmon .................. G10L 21/06 235/462.44 |
| 6,418,179 | B1 | | 7/2002 | Shieh |
| 6,582,329 | B1 | | 6/2003 | Cabrera |
| 7,437,776 | B1 | | 10/2008 | Brown |
| 7,442,133 | B2 | | 10/2008 | Wolf |
| 8,043,173 | B2 | | 10/2011 | Menalagha et al. |
| 8,221,253 | B2 | | 7/2012 | Lidenberg |
| 8,414,430 | B2 | * | 4/2013 | McKinley .......... A63B 21/0555 2/161.1 |
| 9,079,092 | B2 | | 7/2015 | Stack |
| D787,515 | S | * | 5/2017 | Friedman .................... D14/388 |
| 10,034,622 | B1 | | 7/2018 | Mahmoud |
| 10,434,393 | B2 | * | 10/2019 | Young ............... A63B 69/0071 |
| 2010/0077532 | A1 | | 4/2010 | Kettani |
| 2010/0156783 | A1 | * | 6/2010 | Bajramovic ............ G06F 1/163 345/156 |
| 2010/0311546 | A1 | * | 12/2010 | Kupferman ........ A63B 21/0004 482/47 |
| 2012/0056805 | A1 | * | 3/2012 | Bronner, Sr. ........... G06F 3/014 345/157 |
| 2015/0190246 | A1 | * | 7/2015 | Ryu ....................... G06F 3/011 74/89.22 |
| 2017/0168586 | A1 | | 6/2017 | Sinha et al. |
| 2017/0319934 | A1 | | 11/2017 | Horne |
| 2018/0028890 | A1 | | 2/2018 | Frugoli |
| 2019/0022495 | A1 | | 1/2019 | Neale et al. |

OTHER PUBLICATIONS

Rabya Bahadur, A. Mahmood, Prosthetic hand module using electromechanical actuators: A simulation, IEEE Xplore, Feb. 6, 2017, 5 pages, https://ieeexplore.ieee.org/document/7840124, IEEE, Islamabad, Pakistan.

Hillary Sanctuary, Feedback enhances brainwave control of a novel hand-exoskeleton, Jan. 22, 2018, 4 pages https://actu.epfl.ch/news/feedback-enhances-brainwave-control-of-a-novel-han/ EPFL-Media.com, CH-1015 Lausanne, Switzerland.

* cited by examiner

Practice Aid Device

Control System

PRACTICE AID DEVICE FOR PERFORMANCE FEEDBACK AND HAND AND FINGER POSITIONING TRAINING DURING SPORTS PLAY

CROSS-REFERENCE TO RELATED APPLICATIONS

N/A.

FIELD OF THE INVENTION

The present invention relates generally to the field of systems and methods for sports practice, and more particularly to methods and systems for practicing hand and finger position during sports.

BACKGROUND OF THE INVENTION

In practice of game play of sports requiring handling of a ball, trainers may practice certain positions of hands and fingers, for example relating to setup for a basketball shot for the basket.

However, such conventional hand practice systems are typically complex mechanical systems, which may be disruptive to game play, and may not be effective in accomplishing the trainings goals.

As such, considering the foregoing, it may be appreciated that there continues to be a need for novel and improved devices and methods for practicing hand and finger position during sports.

SUMMARY OF THE INVENTION

The foregoing needs are met, to a great extent, by the present invention, wherein in aspects of this invention, enhancements are provided to the existing model of sports practice aid devices.

In an aspect, a practice aid device can include:
a) a control body, which can be configured to be mounted on a forearm of a user;
b) a plurality of finger control assemblies, which each can include:
   a rotary assembly, which can include:
      a rotatable spool; and
      a rotary actuator, which is connected to the rotatable spool, such that the rotary actuator can be configured to rotate the rotatable spool outward and inward;
   a control cable, such that an inner end of the control cable can be spooled onto the rotatable spool of the rotary assembly, and such that an outer end of the control cable extends from the rotary assembly, such that the outer end of the control cable moves outward when the rotatable spool rotates outward, and such that the outer end of the control cable moves inward when the rotatable spool rotates inward; and
   a finger cap, which can be connected to the outer end of the control cable, such that the finger cap is configured to be mounted on a tip of a finger of the user.

In a related aspect, the practice aid device can further include:
a control unit, which can be configured to control the rotary actuator, such that the rotary actuator rotates the rotatable spool outward and inward according to control signals from the control unit.

In another related aspect, the practice aid device can further include:
a finger strap, which can be connected to the control cable, such that the finger strap is configured to strap around the finger of the user.

In yet a related aspect, the practice aid device can further include:
a first lateral sensor, which is attached to the finger strap; and
a second lateral sensor;
such that the first lateral sensor is configured to measure a first distance between the first and second lateral sensors.

In yet another related aspect, the practice aid device can further include:
a tip tension sensor, which is connected between the finger cap and the control cable, such that the tip tension sensor is configured to measure a pulling force of the control cable.

In a related aspect, the practice aid device can further include:
a front strap, which is connected to the control body, such that the front strap is configured to attach the control body to the forearm of the user; and
a rear strap, which is connected to the control body, such that the rear strap is configured to attach the control body to the forearm of the user.

In a further related aspect, the practice aid device can further include:
a touch screen, which is connected to the control unit, such that the touch screen allows the user to control functions of the practice aid device and review information about finger positions.

In another further related aspect, the practice aid device can further include:
a) a processor;
b) a non-transitory memory;
c) an input/output; and
d) an actuation manager, which can be configured to:
   control outward and inward rotation of each rotary actuator;
   measure an extension of the control cable, in communication with the rotary actuator, in order to determine a position of the finger;
   measure a finger separation distance between a first lateral sensor and a second lateral sensor; and
   measure a pulling force on the control cable in communication with a tip tension sensor; all connected via
e) a data bus.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. In addition, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
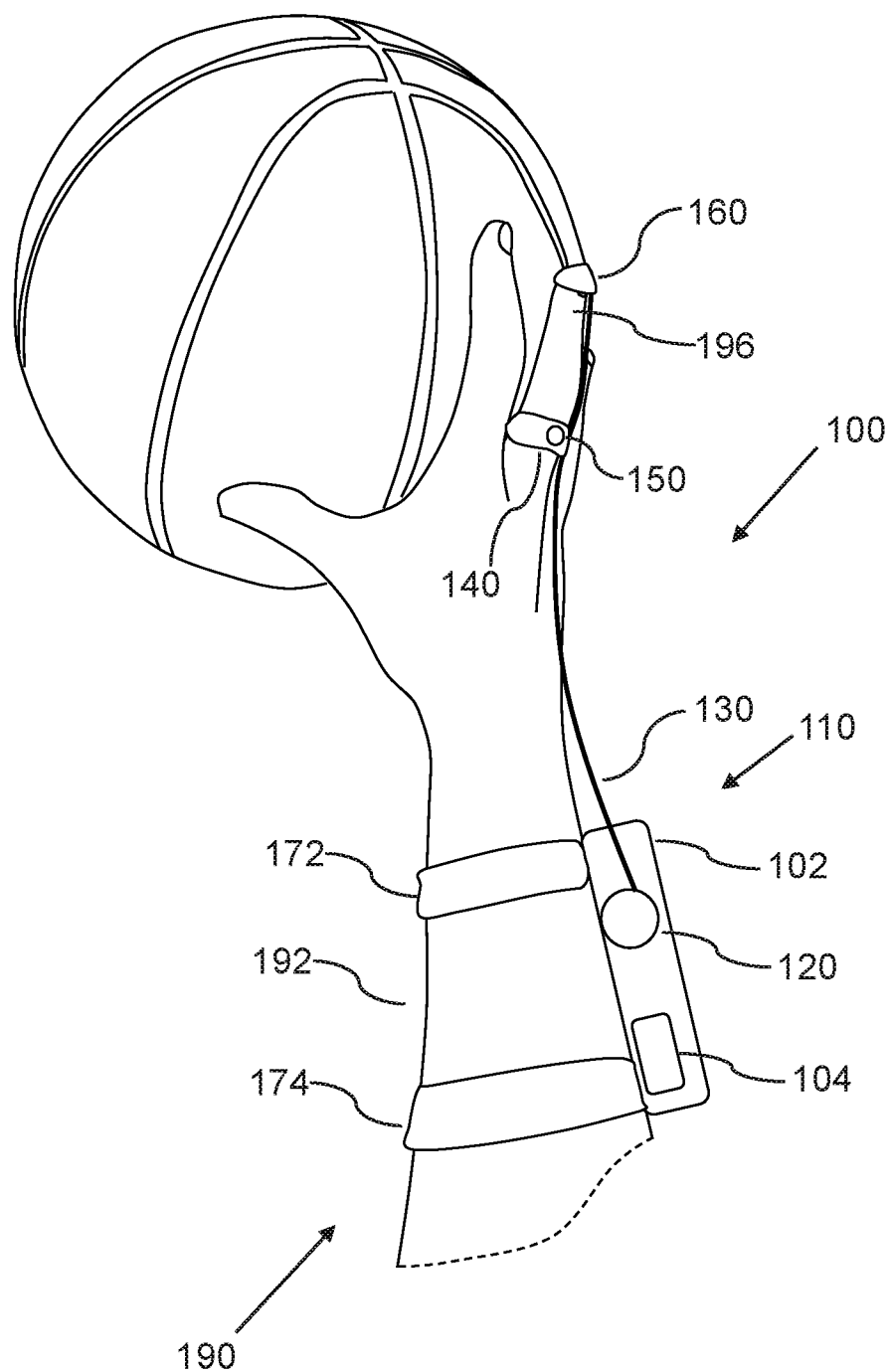
FIG. 1 is a perspective view of a practice aid device in use, according to an embodiment of the invention.

Before describing the invention in detail, it should be observed that the present invention resides primarily in a novel and non-obvious combination of elements and process steps. So as not to obscure the disclosure with details that will readily be apparent to those skilled in the art, certain conventional elements and steps have been presented with lesser detail, while the drawings and specification describe in greater detail other elements and steps pertinent to understanding the invention.

The following embodiments are not intended to define limits as to the structure or method of the invention, but only to provide exemplary constructions. The embodiments are permissive rather than mandatory and illustrative rather than exhaustive.

In the following, we describe the structure of an embodiment of a practice aid device 100 with reference to FIG. 1, in such manner that like reference numerals refer to like components throughout; a convention that we shall employ for the remainder of this specification.

Figure 2A:
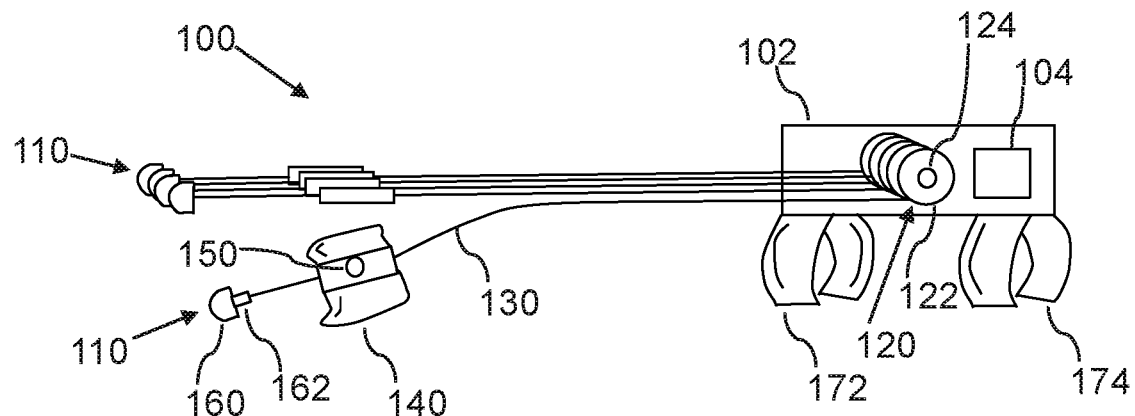
FIG. 2A is a side view of a practice aid device, according to an embodiment of the invention.
Figure 2B:
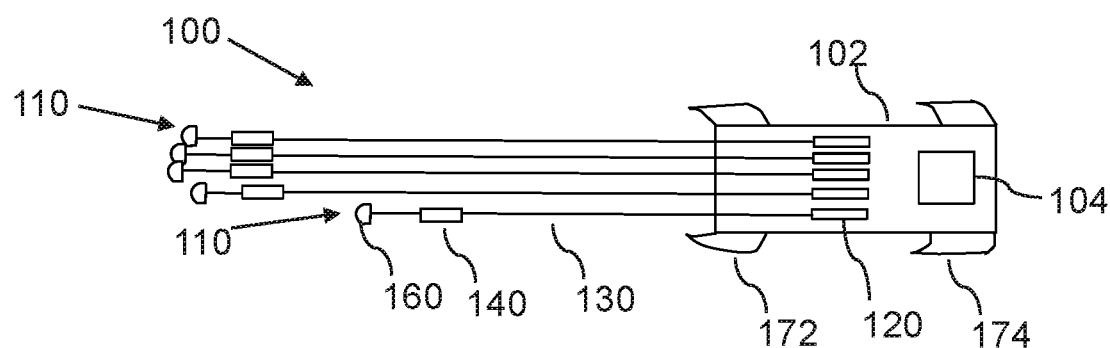
FIG. 2B is a top view of a practice aid device, according to an embodiment of the invention.
Figure 2C:
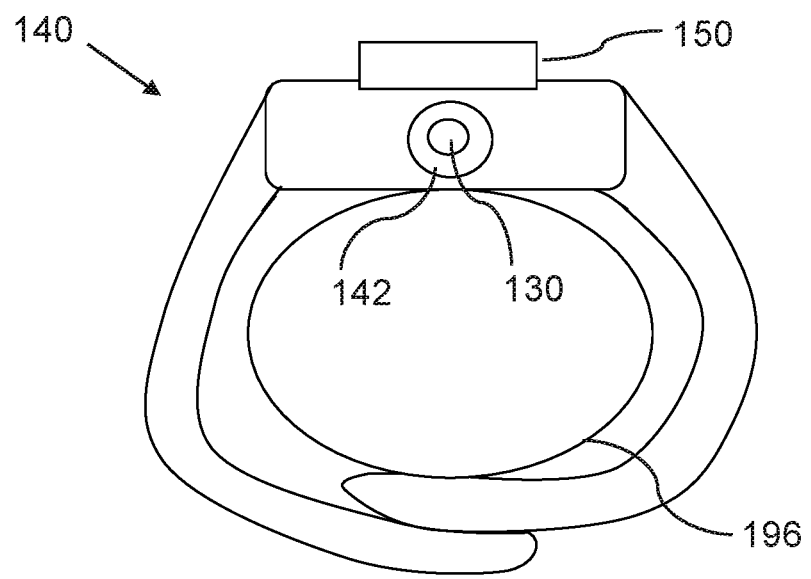
FIG. 2C is a cross-sectional view of a finger strap of a practice aid device, according to an embodiment of the invention.
Figure 5:
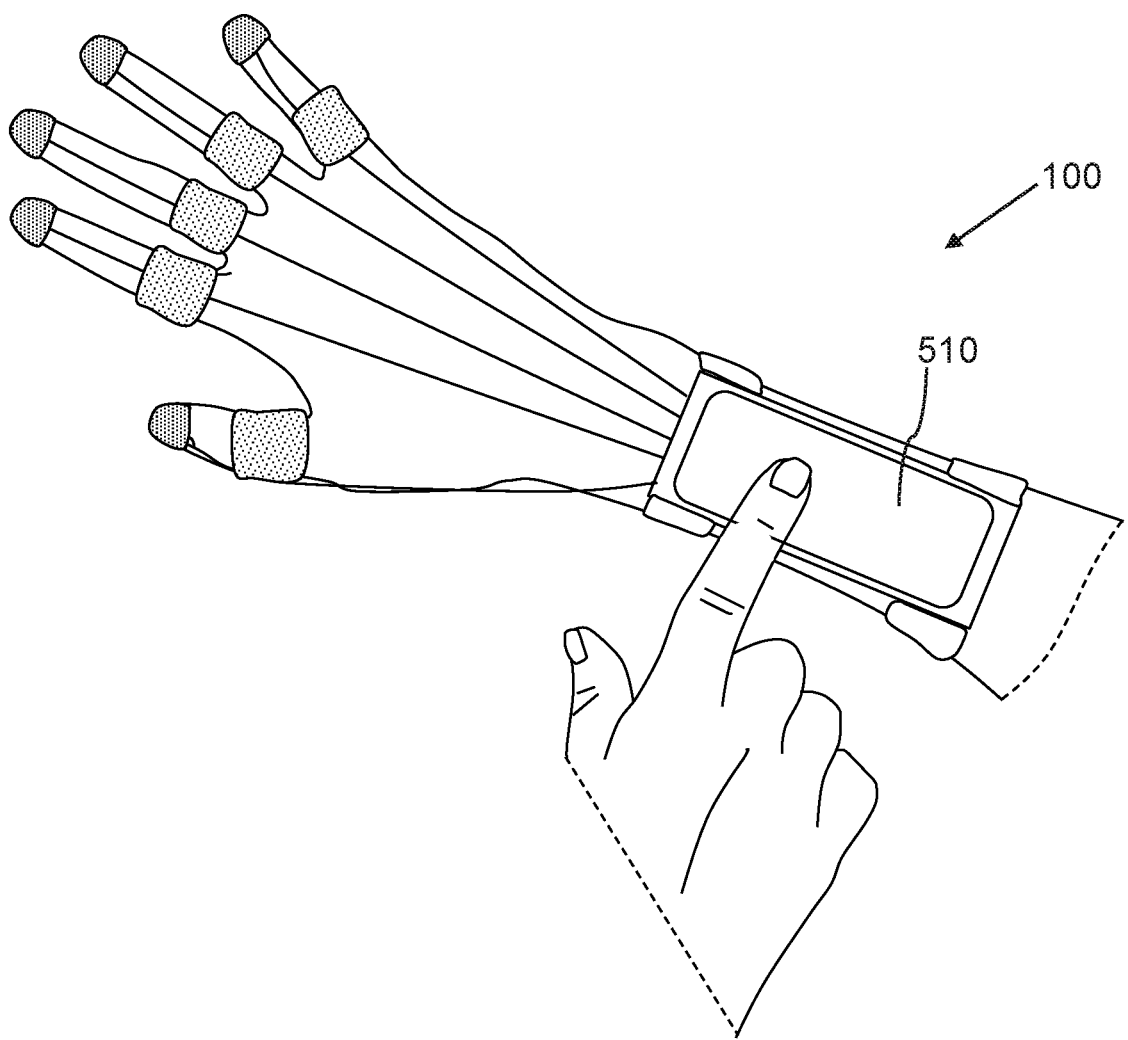
FIG. 5 is a top view of a practice aid system with a screen, according to an embodiment of the invention.

In an embodiment, as shown in FIG. 1, a practice aid device 100 can include:
a) A control body 102, which configured to mount on a forearm 192 of a user 190;
b) A control unit 104;
c) A plurality of finger control assemblies 110, which each can include:
   i. a rotary assembly 120, including:
      1) a rotatable spool 122; and
      2) a rotary actuator 124, which is connected to the rotatable spool 122, such that the rotary actuator 124 can rotate the spool outward and inward according to control signals from the control unit 104;
   ii. a control cable 130, which can be made from a durable and flexible cable material, such that an inner end of the control cable 130 is spooled onto the rotatable spool 122 of the rotary assembly 120, and such that an outer end of the control cable 130 extends from the rotary assembly 120, such that the control cable 130 moves outward when the rotatable spool 122 rotates outward, and such that the control cable 130 moves inward when the rotatable spool 122 rotates inward,
      such that outward movement 322 of the control cable 130 supports closing/clenching movement of the respective finger 196, and such that inward movement 324 of the control cable 130 supports opening/stretching movement of the respective finger 196;
   iii. a finger strap 140, which is connected to the control cable 130, such that the finger strap 140 is configured to strap around a respective finger 196 of the user, for example between the first and second knuckle of the respective finger 196. As shown in FIG. 2C, the finger strap 140 can further include a cable aperture/guide 142, such that the control cable 130 passes through the cable aperture/guide 142, such that the control cable 130 can be aligned with the respective finger 196;
   iv. a first lateral sensor 150, which is attached to the finger strap, such that the first lateral sensor 150 is configured to measure a first/left distance 462 to a second/left lateral sensor 452 and measure a second/right distance 464 to a second/right lateral sensor 454;
   v. A finger cap 160, which is connected to an outer end of the control cable 130, such that the finger cap 160 can be configured to be mounted on a tip of the finger 196 of the user 190;
   vi. a tip tension sensor 162, which is connected between the finger cap and the control cable, such that the tip tension sensor 162 can be configured to measure a tension/pulling force of the control cable 130, which is equivalent to a pressure/force exerted on the tip of the hand by the tip tension sensor 162. The tip tension sensor 162 provides real-time data to the control unit 104 for the purpose of adjusting the finger position and force exerted by the respective finger 196;
b) a front strap 172, which can include a hook and loop fastener on outer ends of the rear strap 174, such that the front strap 172 is used for attaching the practice aid device 100 to a forearm 192 of a user 190, such that the front strap 172 is connected to the control body 102. The front strap 172 can be flexible and adjustable to the individual user's 190 wrist size;
c) a rear strap 174, which can include a hook and loop fastener on outer ends of the rear strap 174, such that the front strap 172 is used for attaching the control body 102 to a forearm 192 of a user 190, such that the rear strap 174 is connected to the control body 102. The rear strap 174 can be flexible and adjustable to the individual user's 190 wrist size; and d) a touch screen 510, which is connected to the control unit 104, such that the touch screen 510 allows the user 190 to control functions of the practice aid device 100 and review information about finger positions during gameplay, as shown in FIG. 5;

whereby the practice aid device 100 can implement wire tension control, digital actuation and/or exoskeletal extension/retraction for each finger of a hand.

In a related embodiment, the lateral sensor 150, 452, 454 can be a proximity sensor 150, 452, 454, such as a capacitive, inductive or magnetic proximity sensor, configured to measure a distance between any pair of proximity sensors 150, 452, 454.

In another related embodiment, the plurality of finger control assemblies can further include:

a first finger control assembly, comprising:
  a second control cable;
  a first finger strap, which is connected to the second control cable, such that the finger strap is configured to strap around a first finger of the user; and
  a first lateral sensor, which is attached to the first finger strap; and a second finger control assembly, comprising:
  a third control cable;
  a second finger strap, which is connected to the third control cable, such that the finger strap is configured to strap around a second finger of the user; and
  a second lateral sensor, which is attached to the second finger strap;

such that the control unit is configured to measure a first distance between the first and second lateral sensors.

In another related embodiment, as shown in FIGS. 2A-2B, 3A-3B, and 4-5, the practice aid device 100 can include five finger control assemblies 110, one finger control assembly 110 for each finger of the hand.

In a related embodiment, the tip tension sensor 162 can be a force gauge 162, such as a load cell 162, which converts a pulling force into an electrical signal which is received by the control unit 104. Alternatively, the tip tension sensor 162 can be a stretch sensor 162 or a tension meter 164, or some other type of gauge for measuring tension/force applied.

Figure 6:
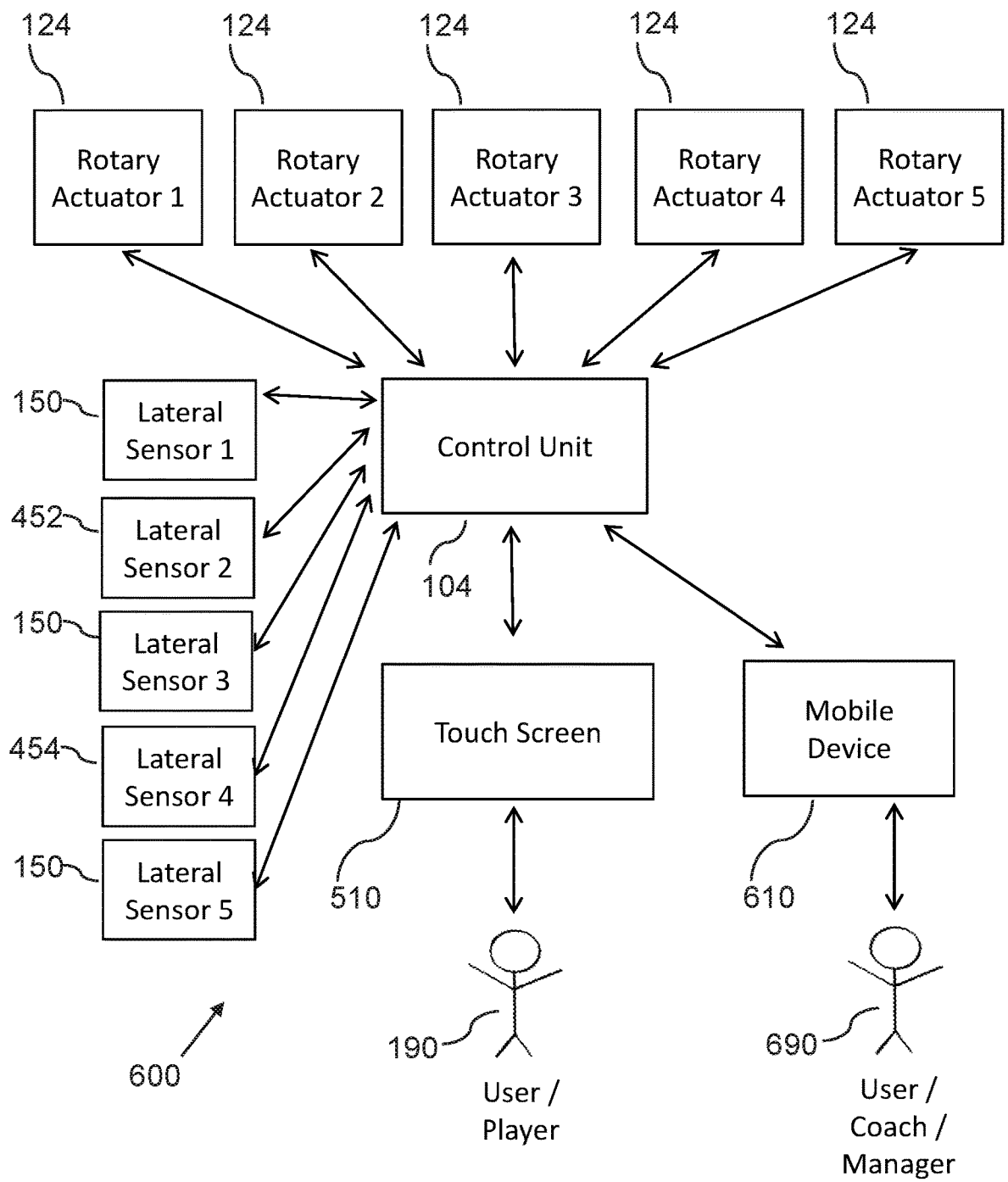
FIG. 6 is a schematic diagram illustrating a control unit of the practice aid device, according to an embodiment of the invention.

In a related embodiment, as shown in FIG. 6, a control system 600 of the practice aid device 100 can include:
a) five rotary actuators 124;
b) five lateral sensors 150, 452, 454;
c) a control unit 104, which controls rotation of the five rotary actuators 124; and
d) a touch screen 510, which is connected to the control unit 104, such that the touch screen 510 allows the user 190 to control functions of the practice aid device 100.

In a further related embodiment, the control unit 104 can be configured with voice recognition to accept voice commands from the user 190 to control functions of the practice aid device 100.

In another further related embodiment, a coach 690 or manager 690 can communicate with the practice aid device 100 via a mobile device 610, to control functions of the practice aid device 100. The mobile device 610 can for example be a smartphone, tablet, or a practice aid device 100 worn by the coach 690.

Figure 7:
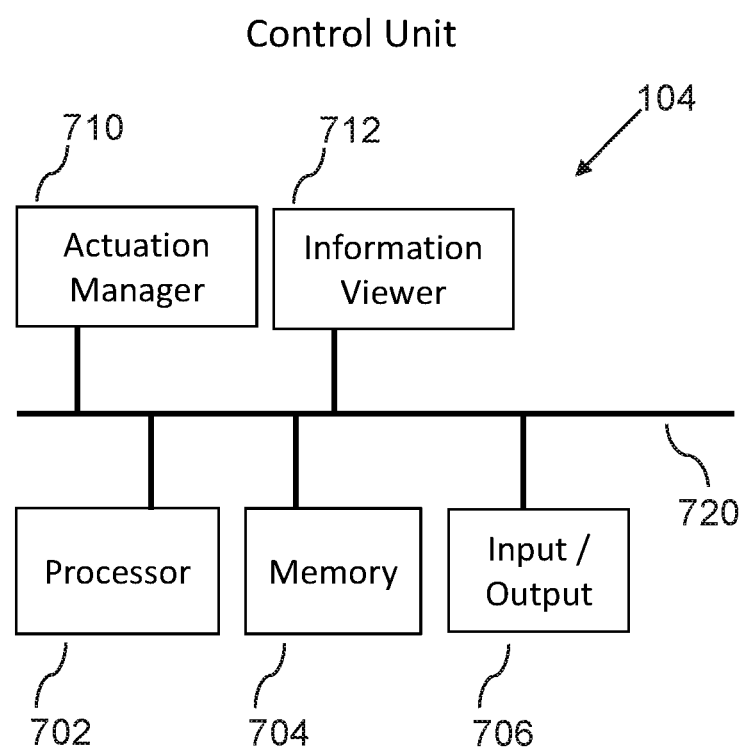
FIG. 7 is a flowchart illustrating steps that may be followed, in accordance with one embodiment of a method or process of practice aid.

In a related embodiment, as shown in FIG. 7, a control unit 104 can include:
a) A processor 702;
b) A non-transitory memory 704;
c) An input/output 706;
d) An actuation manager 710, which is configured to:
  i. control outward and inward rotation 312, 314 of each rotary actuator 124;
  ii. measure an extension 322, 324 of each control cable 130 in communication with a respective rotary actuator 124, in order to determine a position of a finger 196;
  iii. measure a finger separation distance 462, 464 between a first lateral sensor 150 and a second lateral sensor 452, 454, such that a distance from a first finger to any second finger can be calculated; and
  iv. measure a pulling force 322, 324 on the control cable 130 in communication with a tip tension sensor 162;
e) An information viewer 712, which is configured to enable a user to browse information concerning the finger extension/position, finger separation, and pulling force; all connected via
f) A data bus 720.

Figure 3A:
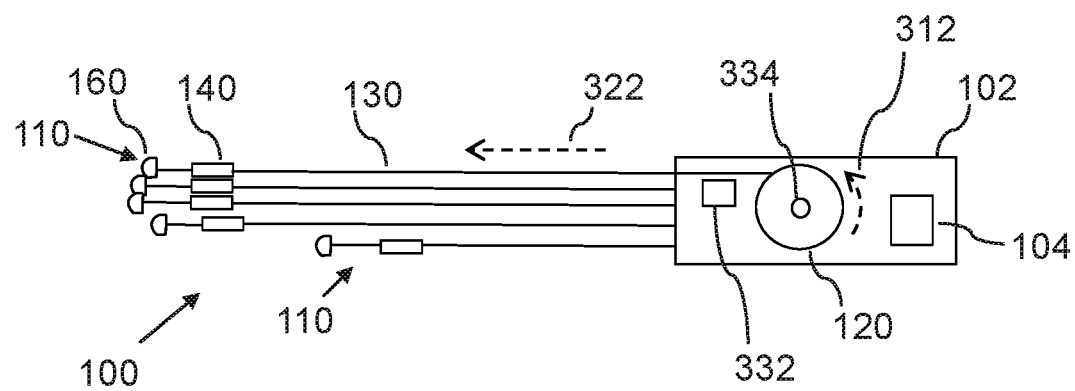
FIG. 3A is a top view of a practice aid device showing an inward movement of a rotary actuator, according to an embodiment of the invention.
Figure 3B:
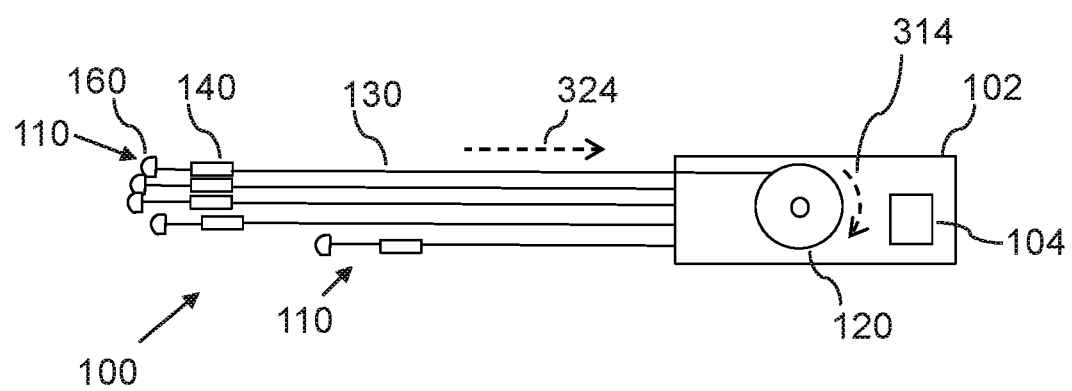
FIG. 3B is a top view of a practice aid device showing an outward movement of a rotary actuator, according to an embodiment of the invention.
Figure 4:
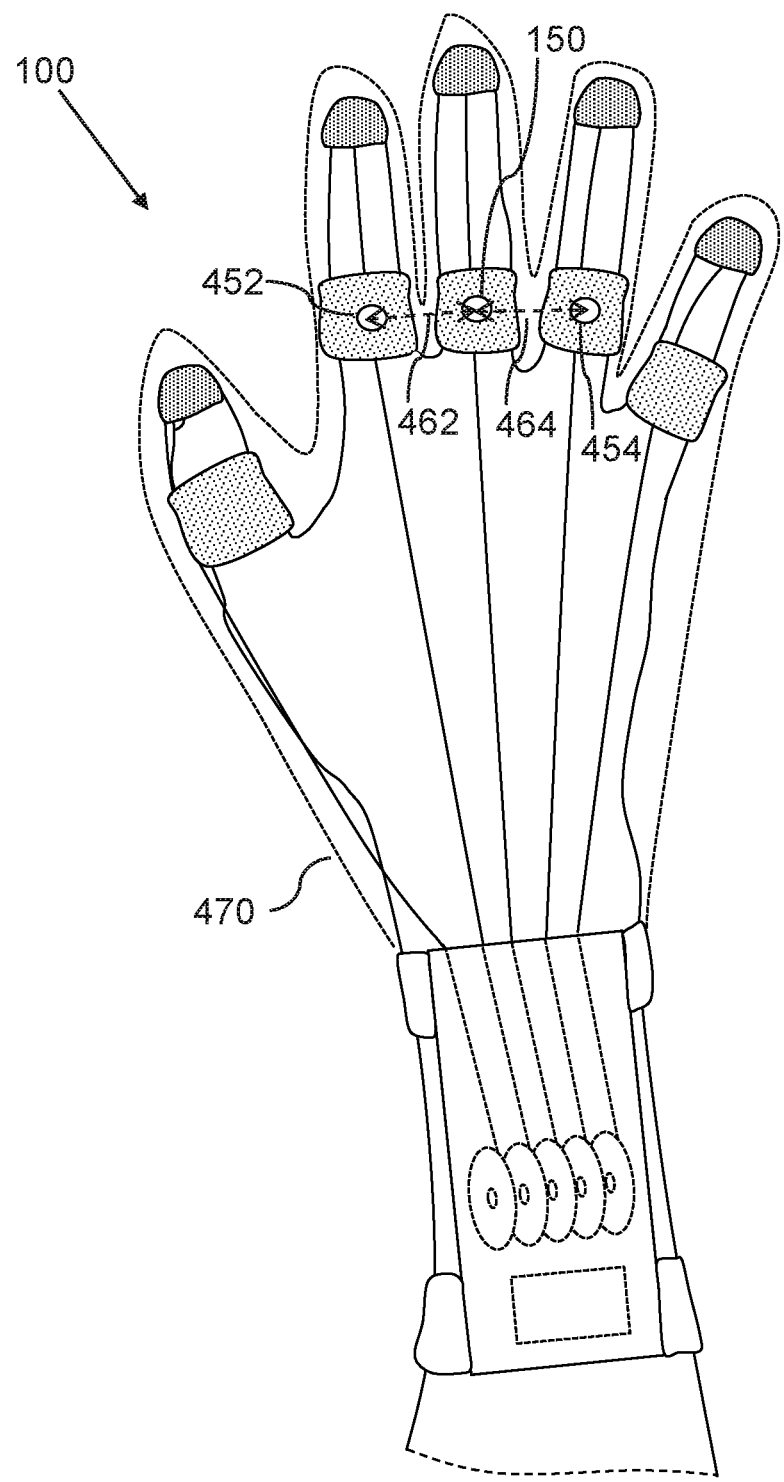
FIG. 4 is a top view of a practice aid device mounted on a forearm and hand of a user, according to an embodiment of the invention.

In a related embodiment, as shown in FIG. 3A, each finger control assembly 110 can further include: a cable sensor 332 334, which is configured to measure an extraction/extension length 322, 324 of the control cable 130; and In related embodiments, the cable sensor 332 can be configured as a rotation sensor 332, such as for example manufactured by ALTHERIS™ Sensor & Control, which is configured to measure a rotation of the rotary assembly 120, which is proportional to an extraction length 322, 324, such that the actuation manager 710 is configured to calculate the extraction length 322, 324 based on the rotation of the rotary assembly 120.

In related embodiments, the cable sensor 334 can be configured as an optical sensor 334, which can be a led sensor or a laser sensor, including a light source and a light detector, such as for commonly used in an optical computer mouse, which is configured to measure a movement of the control cable 130, wherein the movement is directly proportional to an extraction length 322, 324, such that the actuation manager 710 is configured to calculate the extraction length 946 based on the movement of the control cable 130.

In related embodiment, the actuation manager 710 can be configured to calibrate the practice aid device 100 by registering a fully extended position of each rotary actuator 124, when the hand of the user is in a closed (i.e. clenched) position; and by registering a fully retracted position of each rotary actuator 124, when the hand of the user is in an open (i.e. stretched) position.

In related embodiment, the actuation manager 710 can be configured to calibrate the practice aid device 100 by registering a minimal distance between fingers of a hand, when the fingers of the user are in a assembled/tight position; and by registering a maximal distance between the fingers, when the fingers of the user are in a spread/wide position.

In a related embodiment, the practice aid device 100 can further include an outer flexible structure 470, which can be a glove 470, such that the mechanical components of the practice aid device 100 can be mounted/housed in the outer flexible structure 470.

In related embodiments, the practice aid device 100 can be used for basketball and other sports requiring training of hand positions and perfecting hand movement, such as for example baseball, American football, tennis, etc. The practice aid device 100 can also be programmed to aid in pre-practice hand exercises and hand stretches. The practice aid device 100 can function as a training aid and promote athletic development by developing muscle memory through repetition In a related embodiment, the tip tension sensor 162 provides pressure feedback to the control unit 104 in order to control the rotary assembly 120 maintaining a constant retracted pressure to hold the desired hand position. The rotary assembly 120 releases the control cable 130 to return the finger to a resting or natural static position. The practice aid device 100 may be configured with cutout area or apertures of a glove to allow for human touch perception by a user.

In related embodiments, the lateral sensors 150 provide real-time finger separation/distance data and allows the control unit 104 to adjust the space between fingers with the use of an electro-magnetic distance measuring algorithm. This data can be specific to the individual athlete profile and can be adjusted respectively to the user's physical size.

In related embodiments, the practice aid device 100 can be designed to maintain a number of athlete profiles, which are selectable and adjustable through the touch screen 510 or other defined interface devices.

In other related embodiments, the practice aid device 100 can allow the user to decide what sport and/or athlete to practice with, such that targeted finger positions, separation and tension can be customized for the particular sport and athlete. Thereby a user can align his or her practices across many sporting fields and practice with different players to find the best sporting fit.

In other related embodiments, the practice aid device 100 can detect its position on a specified court. The practice aid device 100 can heat up, vibrate or light up whenever a user is in their predetermined playing position or hot spot.

In related embodiments, the practice aid device 100 can accommodate the users best form and success rate data into a recommended user profile. This can be enhanced to provide profiles for differing positions during a game or based on court position.

In related embodiments, the practice aid device 100 can aid in tracking shot makes and misses, for example by detecting a predetermined hand position and hand movement associated with a shot.

In yet other related embodiments, the practice aid device 100 can be capable of detecting and analyzing hand motion data in an effort to make performance recommendations and suggested profile updates through collected data.

FIGS. 1-7 are block diagrams and flowcharts, methods, devices, systems, apparatuses, and computer program products according to various embodiments of the present invention. It shall be understood that each block or step of the block diagram, flowchart and control flow illustrations, and combinations of blocks in the block diagram, flowchart and control flow illustrations, can be implemented by computer program instructions or other means. Although computer program instructions are discussed, an apparatus or system according to the present invention can include other means, such as hardware or some combination of hardware and software, including one or more processors or controllers, for performing the disclosed functions.

In this regard, FIGS. 1-7 depict the computer devices of various embodiments, each containing several of the key components of a general-purpose computer by which an embodiment of the present invention may be implemented. Those of ordinary skill in the art will appreciate that a computer can include many components. However, it is not necessary that all of these generally conventional components be shown in order to disclose an illustrative embodiment for practicing the invention. The general-purpose computer can include a processing unit and a system memory, which may include various forms of non-transitory storage media such as random access memory (RAM) and read-only memory (ROM). The computer also may include nonvolatile storage memory, such as a hard disk drive, where additional data can be stored.

It shall be understood that the above-mentioned computing components of the control unit 104 are to be interpreted in the most general manner.

For example, the processor 702 can include a single physical microprocessor or microcontroller, a cluster of processors, a datacenter or a cluster of datacenters, a computing cloud service, and the like.

In a further example, the non-transitory memory 704 can include various forms of non-transitory storage media, including random access memory and other forms of dynamic storage, and hard disks, hard disk clusters, cloud storage services, and other forms of long-term storage. Similarly, the input/output 706 can include a plurality of well-known input/output devices, such as screens, keyboards, pointing devices, motion trackers, communication ports, and so forth.

Furthermore, it shall be understood that the control unit 104 can include a number of other components that are well known in the art of general computer devices, and therefore shall not be further described herein. This can include system access to common functions and hardware, such as for example via operating system layers such as WINDOWS™, LINUX™, and similar operating system software, but can also include configurations wherein application services are executing directly on server hardware or via a hardware abstraction layer other than a complete operating system.

An embodiment of the present invention can also include one or more input or output components, such as a mouse, keyboard, monitor, and the like. A display can be provided for viewing text and graphical data, as well as a user interface to allow a user to request specific operations. Furthermore, an embodiment of the present invention may be connected to one or more remote computers via a network interface. The connection may be over a local area network (LAN) wide area network (WAN), and can include all of the necessary circuitry for such a connection.

Typically, computer program instructions may be loaded onto the computer or other general-purpose programmable machine to produce a specialized machine, such that the instructions that execute on the computer or other programmable machine create means for implementing the functions specified in the block diagrams, schematic diagrams or flowcharts. Such computer program instructions may also be stored in a computer-readable medium that when loaded into a computer or other programmable machine can direct the machine to function in a particular manner, such that the instructions stored in the computer-readable medium produce an article of manufacture including instruction means that implement the function specified in the block diagrams, schematic diagrams or flowcharts.

In addition, the computer program instructions may be loaded into a computer or other programmable machine to cause a series of operational steps to be performed by the computer or other programmable machine to produce a computer-implemented process, such that the instructions that execute on the computer or other programmable machine provide steps for implementing the functions specified in the block diagram, schematic diagram, flowchart block or step.

Accordingly, blocks or steps of the block diagram, flowchart or control flow illustrations support combinations of means for performing the specified functions, combinations of steps for performing the specified functions and program instruction means for performing the specified functions. It will also be understood that each block or step of the block diagrams, schematic diagrams or flowcharts, as well as combinations of blocks or steps, can be implemented by special purpose hardware-based computer systems, or combinations of special purpose hardware and computer instructions, that perform the specified functions or steps.

As an example, provided for purposes of illustration only, a data input software tool of a search engine application can be a representative means for receiving a query including one or more search terms. Similar software tools of applications, or implementations of embodiments of the present invention, can be means for performing the specified functions. For example, an embodiment of the present invention may include computer software for interfacing a processing element with a user-controlled input device, such as a mouse, keyboard, touch screen display, scanner, or the like. Similarly, an output of an embodiment of the present invention may include, for example, a combination of display software, video card hardware, and display hardware. A processing element may include, for example, a controller or microprocessor, such as a central processing unit (CPU), arithmetic logic unit (ALU), or control unit.

Here has thus been described a multitude of embodiments of the practice aid device 100, and methods related thereto, which can be employed in numerous modes of usage.

The many features and advantages of the invention are apparent from the detailed specification, and thus, it is intended by the appended claims to cover all such features and advantages of the invention, which fall within the true spirit and scope of the invention.

Many such alternative configurations are readily apparent, and should be considered fully included in this specification and the claims appended hereto. Accordingly, since numerous modifications and variations will readily occur to those skilled in the art, the invention is not limited to the exact construction and operation illustrated and described, and thus, all suitable modifications and equivalents may be resorted to, falling within the scope of the invention.

What is claimed is:

1. A practice aid device, comprising:
a) a control body, which is configured to be mounted on a forearm of a user; and
b) a plurality of finger control assemblies, each comprising:
a rotary assembly, comprising:
a rotatable spool; and
a rotary actuator, which is connected to the rotatable spool, such that the rotary actuator is configured to rotate the rotatable spool outward and inward;
a first control cable, such that an inner end of the first control cable is spooled onto the rotatable spool of the rotary assembly, and such that an outer end of the first control cable extends from the rotary assembly, such that the outer end of the first control cable moves outward when the rotatable spool rotates outward, and such that the outer end of the first control cable moves inward when the rotatable spool rotates inward; and
a finger cap, which is connected to the outer end of the first control cable, such that the finger cap is configured to be mounted on a tip of a respective finger of the user.

2. The practice aid device of claim 1, further comprising:
a control unit, which is configured to control the rotary actuator, such that the rotary actuator rotates the rotatable spool outward and inward according to control signals from the control unit.

3. The practice aid device of claim 2, further comprising:
a touch screen, which is connected to the control unit, such that the touch screen allows the user to control functions of the practice aid device and review information about finger positions.

4. The practice aid device of claim 2, further comprising:
a) a processor;
b) a non-transitory memory;
c) an input/output; and
d) an actuation manager, which is configured to:
control outward and inward rotation of each rotary actuator;
measure an extension of the first control cable, in communication with the rotary actuator, in order to determine a position of the respective finger;
measure a finger separation distance between a first lateral sensor and a second lateral sensor; and
measure a pulling force on the first control cable in communication with a tip tension sensor; all connected via
e) a data bus.

5. The practice aid device of claim 1, further comprising:
a finger strap, which is connected to the first control cable, such that the finger strap is configured to strap around the respective finger of the user.

6. The practice aid device of claim 5, wherein the finger strap further comprises a cable aperture, such that the first control cable passes through the cable aperture, such that the first control cable is aligned with the respective finger.

7. The practice aid device of claim 1, further comprising a control unit; and
wherein the plurality of finger control assemblies further comprises:
a first finger control assembly, comprising:
a second control cable;
a first finger strap, which is connected to the second control cable, such that the finger strap is configured to strap around a first finger of the user; and
a first lateral sensor, which is attached to the first finger strap; and
a second finger control assembly, comprising:
a third control cable;
a second finger strap, which is connected to the third control cable, such that the finger strap is configured to strap around a second finger of the user; and
a second lateral sensor, which is attached to the second finger strap;
such that the control unit is configured to measure a first distance between the first and second lateral sensors.

8. The practice aid device of claim 1, further comprising:
a tip tension sensor, which is connected between the finger cap and the first control cable, such that the tip tension sensor is configured to measure a pulling force of the first control cable.

9. The practice aid device of claim 1, further comprising:
a front strap, which is connected to the control body, such that the front strap is configured to attach the control body to the forearm of the user; and
a rear strap, which is connected to the control body, such that the rear strap is configured to attach the control body to the forearm of the user.

10. The practice aid device of claim 1, wherein the plurality of finger control assemblies comprises five finger control assemblies.

11. A practice aid device, comprising:
at least one finger control assembly, comprising:
a rotary assembly, comprising:
a rotatable spool; and
a rotary actuator, which is connected to the rotatable spool, such that the rotary actuator is configured to rotate the rotatable spool outward and inward;
wherein the rotary assembly is configured to be mounted on a forearm of a user;
a first control cable, such that an inner end of the first control cable is spooled onto the rotatable spool of the rotary assembly, and such that an outer end of the first control cable extends from the rotary assembly, such that the outer end of the first control cable moves outward when the rotatable spool rotates outward, and such that the outer end of the first control cable moves inward when the rotatable spool rotates inward; and
a finger cap, which is connected to the outer end of the first control cable, such that the finger cap is configured to be mounted on a tip of a respective finger of the user.

12. The practice aid device of claim 11, further comprising:
a control unit, which is configured to control the rotary actuator, such that the rotary actuator rotates the rotatable spool outward and inward according to control signals from the control unit.

13. The practice aid device of claim 12, further comprising:
a touch screen, which is connected to the control unit, such that the touch screen allows the user to control functions of the practice aid device and review information about finger positions.

14. The practice aid device of claim 11, further comprising:
a finger strap, which is connected to the first control cable, such that the finger strap is configured to strap around the respective finger of the user.

15. The practice aid device of claim 14, wherein the at least one finger control assembly further comprises:
a first finger control assembly, comprising:
a second control cable;
a first finger strap, which is connected to the second control cable, such that the finger strap is configured to strap around a first finger of the user; and
a first lateral sensor, which is attached to the first finger strap; and
a second finger control assembly, comprising:
a third control cable;
a second finger strap, which is connected to the third control cable, such that the finger strap is configured to strap around a second finger of the user; and
a second lateral sensor, which is attached to the second finger strap;
such that the first lateral sensor is configured to measure a first distance between the first and second lateral sensors.

16. The practice aid device of claim 14, wherein the finger strap further comprises a cable aperture, such that the first control cable passes through the cable aperture, such that the first control cable is aligned with the respective finger.

17. The practice aid device of claim 11, further comprising:
a tip tension sensor, which is connected between the finger cap and the first control cable, such that the tip tension sensor is configured to measure a pulling force of the first control cable.

18. The practice aid device of claim 11, further comprising:
a front strap, which is connected to the at least one finger control assembly, such that the front strap is configured to attach the at least one finger control assembly to the forearm of the user; and
a rear strap, which is connected to the at least one finger control assembly, such that the rear strap is configured to attach the at least one finger control assembly to the forearm of the user.

19. The practice aid device of claim 11, further comprising:
a) a processor;
b) a non-transitory memory;
c) an input/output; and
d) an actuation manager, which is configured to:
control outward and inward rotation of each rotary actuator;
measure an extension of the first control cable, in communication with the rotary actuator, in order to determine a position of the respective finger;
measure a finger separation distance between a first lateral sensor and a second lateral sensor; and
measure a pulling force on the first control cable in communication with a tip tension sensor; all connected via
e) a data bus.

20. The practice aid device of claim 11, wherein the at least one finger control assembly comprises five finger control assemblies.

* * * * *